United States Patent [19]

Lopez

[11] 4,432,764

[45] Feb. 21, 1984

[54] ANTISEPTIC END CAP FOR CATHETER

[75] Inventor: Georges Lopez, Lyons, France

[73] Assignee: Societe de Materials Annexed de Dialyse S.M.A.D., France

[21] Appl. No.: 318,271

[22] Filed: Nov. 4, 1981

[30] Foreign Application Priority Data

Nov. 5, 1980 [FR] France ................ 80 23950

[51] Int. Cl.³ ........................................ A61M 25/00
[52] U.S. Cl. ........................................ 604/283; 604/905
[58] Field of Search ........... 128/349, 348, 217, 313 A, 128/219, 214.2, 218.5, 224, 247; 422/301, 302; 222/390; 604/132, 212, 217, 236, 238, 280, 283, 905

[56] References Cited

U.S. PATENT DOCUMENTS

| | | | |
|---|---|---|---|
| 2,816,550 | 12/1957 | Hudson | 128/213 X |
| 2,877,810 | 3/1959 | Zackheim | 604/217 X |
| 2,948,279 | 8/1960 | Mann | 604/212 X |
| 3,766,919 | 10/1973 | Cloyd | 128/220 |
| 4,209,013 | 6/1980 | Alexander et al. | 128/213 A |
| 4,324,239 | 4/1982 | Gordon et al. | 604/283 X |
| 4,360,024 | 11/1982 | Wallace | 604/283 |

*Primary Examiner*—Stephen C. Pellegrino
*Attorney, Agent, or Firm*—Karl F. Ross; Herbert Dubno

[57] ABSTRACT

An antisepticizing device comprises a cap having a formation adapted to fit complementarily with the end fitting of the catheter and formed with a passage having one end communicating with the end fitting and therethrough with the catheter when the end fitting is fitted to the formation. A reservoir in the cap has a movable wall, and the other end of the passage opens into the reservoir which contains a body of an antiseptic liquid. The movable wall of the reservoir can be displaced to force the liquid through the passage into the catheter fitted to the formation. This movable wall can be formed as a piston slidable in the reservoir and having the formation and passage. The end fitting and cap have complementary screwthreads.

10 Claims, 8 Drawing Figures

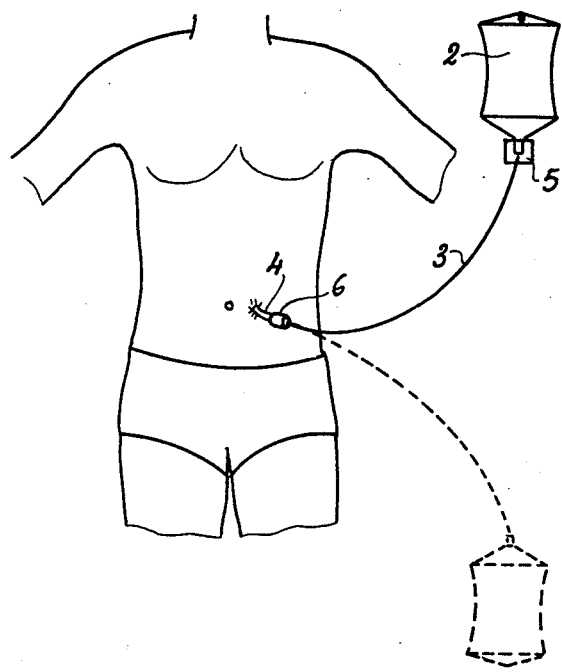
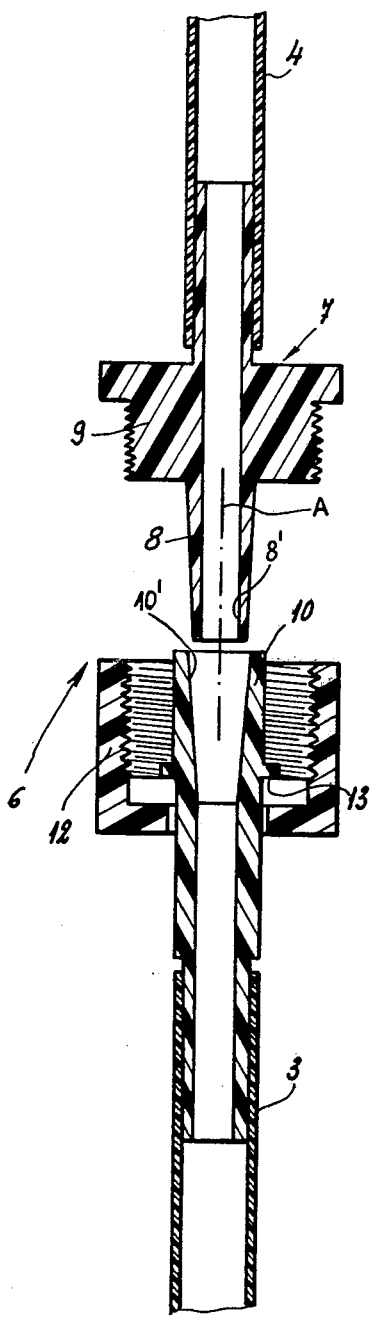
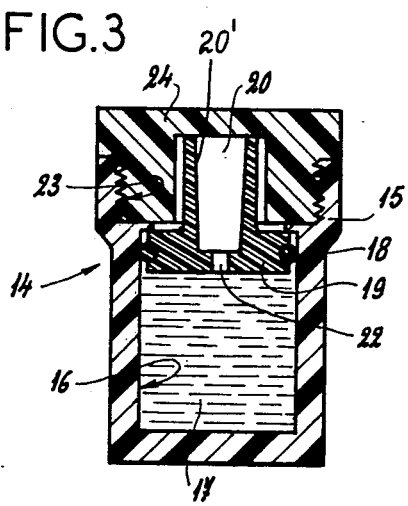

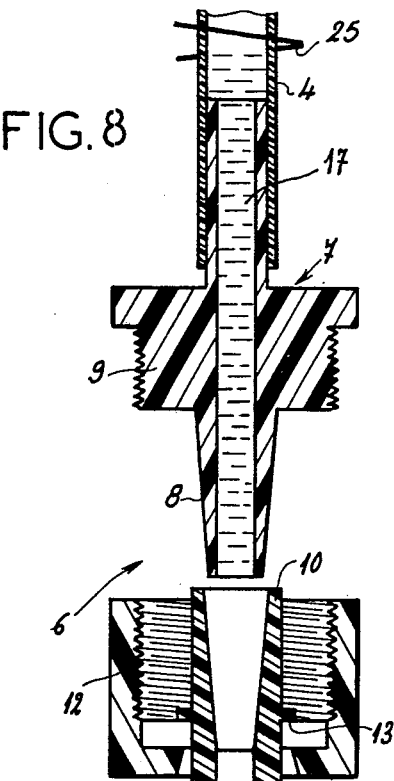
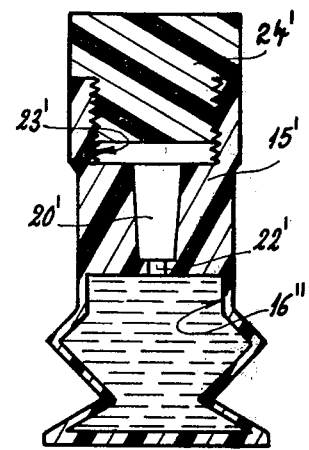
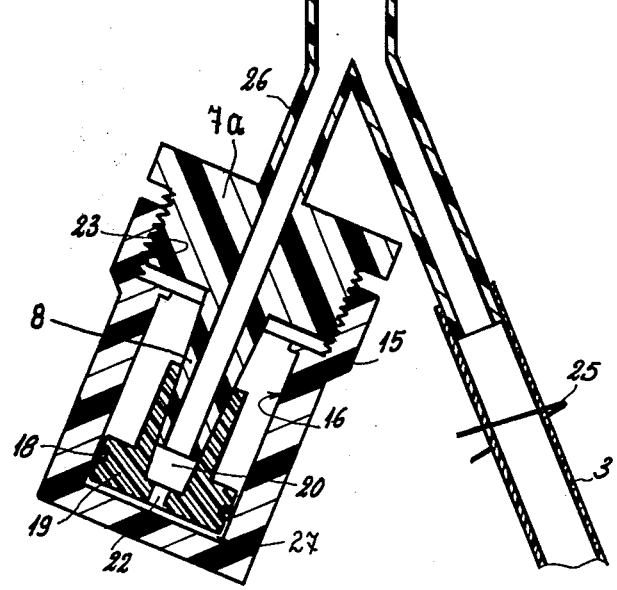

ANTISEPTIC END CAP FOR CATHETER

FIELD OF THE INVENTION

The present invention relates to an end cap for a catheter. More particularly this invention concerns such an end cap used for antisepticizing the end fitting of a permanently implanted catheter.

BACKGROUND OF THE INVENTION

Various serious medical treatments require the use of a permanently implanted catheter having an end fitting that is connected periodically or continuously to a machine, liquid-supply reservoir, or liquid-receiving reservoir. Obviously it is essential that the connection be made aseptically, particularly as the person undergoing such treatment is frequently in a fragile state of health. Even the slightest sepsis can introduce bacteria directly into the body of the patient, creating the possibility of a grave infection.

There are two main types of peritoneal dialysis where such a catheter having such an end fitting is used, namely iterative peritoneal dialysis and continuous ambulatory peritoneal dialysis. The first type is carried out mainly in a hospital or clinic using machines that are connected to the patient's catheter for the treatment. The second type involves a connection made to the patient's catheter from a pouch supply carried directly on the patient.

The problem with a method such as continuous ambulatory peritoneal dialysis is that the septic problem must be taken care of by the patient rather than by trained medical personnel. Obviously in such a situation experience has shown a great number of infections caused by aseptic procedures. The main problem is normally caused at the connection to the end fitting of the implanted catheter. The connection must seal perfectly, not allowing any foreign matter to enter the liquid stream which must pass through it, and must of course also prevent this liquid from leaking out. Furthermore this connection must be mechanically very strong so that it cannot be accidentally pulled open.

The connection must in addition be relatively easy to do and undo, without the user's fingers having to touch any of the vital inner parts. The pouch/reservoir of dialysis liquid and its tube and connector are of course provided in a sterile packing, and the user must be able to connect it up without touching anything that itself will come into contact with the stream of liquid being passed through the catheter into his or her body.

OBJECTS OF THE INVENTION

It is therefore an object of the present invention to provide an improved antiseptic catheter fitting.

Another object is the provision of such an antiseptic catheter fitting which overcomes the above-given disadvantages.

Yet another object is to provide a device for antisepticizing an end fitting of an implanted catheter of the type used for peritoneal dialysis.

SUMMARY OF THE INVENTION

These objects are attained according to the instant invention in an antisepticizing device comprising a cap having a formation adapted to fit complementarily with the end fitting of the catheter and formed with a passage having one end communicating with the end fitting and therethrough with the catheter when the end fitting is fitted to the formation. A reservoir in the cap has a movable wall, and the other end of the passage opens into this reservoir which contains a body of an antiseptic liquid. Means is provided for displacing the movable wall of the reservoir and thereby forcing the liquid through the passage into the catheter fitted to the formation.

The system according to the instant invention is therefore self-sterilizing or self-antisepticizing. It virtually cleans itself with each use so as to leave the catheter end fitting perfectly aseptic.

In accordance with another feature of the invention, the end fitting has a projection and is formed with an external screwthread. The formation of the cap is a recess complementary to the projection, and the cap is formed with an internal screwthread matable with the external screwthread of the fitting to fit the projection into the formation. The connection can therefore be relatively easily screwed together and will be extremely strong once assembled.

The reservoir normally holds a quantity of some 0.5 ml to 1.0 ml of an appropriate liquid antiseptic. When this quantity of liquid is forced into the free end of the catheter it will therefore fill the end portion. If the antiseptic might cause a bad reaction in the body, a clamp can be provided on the catheter between the end fitting and the body to prevent the liquid from entering the body. In any case the movable wall is moved out again before the device is taken off the catheter end fitting to draw out the antiseptic so that virtually none is left in the catheter. This system therefore not only antisepticizes the catheter end each time it is used, but actually cleans up after itself when it is removed. In fact the device according to the instant invention makes the use of an in-line bacteria filter or the like unnecessary, so that it is possible to connect the catheter directly to the solution pouch.

The apparatus according to this invention further comprises a plug having an external thread generally identical to that of the fitting. Thus the cap can be closed by the plug when not in use. This feature also makes the device according to this invention reusable.

According to yet another feature of this invention, the passage is of smaller flow cross section than the catheter. In addition the reservoir may be provided internally with a compressible sponge.

In accordance with a particularly advantageous embodiment of the instant invention, the reservoir is provided with a piston constituting the movable wall. This piston may be manually displaceable to pump the antiseptic liquid into the catheter and draw it out. It is also possible for the piston to be formed with the formation and passage and be displaceable between an outer position close to the internal screwthread and of maximum reservoir volume and an inner position relatively far from the internal screwthread and of minimum reservoir volume. Thus insertion of the fitting into the formation moves the piston from the outer position to the inner position and vice versa. This arrangement is fully automatic, since fitting of the end connection to the device will antisepticize the catheter end and inject a quantity of antiseptic liquid into it and pulling the end connection off the device will automatically draw out this antiseptic liquid.

It is also possible according to this invention for the movable wall of the reservoir to be elastically deformable so that flattening of the reservoir pumps the liquid from the reservoir through the passage. A clip may be provided to hold this reservoir in the flattened condition until the device is taken off, whereupon this clip is removed to allow the reservoir to reassume its original shape and simultaneously suck back in the antiseptic liquid.

According to this invention the end fitting and formation are frustoconical. In addition the fitting, formation, and screwthreads are concentric and coaxial when the fitting is screwed into the cap.

DESCRIPTION OF THE DRAWING

The above and other features and advantages will become more readily apparent from the following, reference being made to the accompanying drawing in which:

FIG. 1 is a front view illustrating the environment of use of the instant invention;

FIG. 2 is a large-scale longitudinal connection through the type of catheter connection for the device of the present invention;

FIG. 3 is a section through the device of the invention;

FIGS. 6 and 7 are views like FIG. 3 but of further devices according to the present invention; and FIG. 8 is a longitudinal section showing another way to use the device of FIG. 3.

SPECIFIC DESCRIPTION

Figure 4:
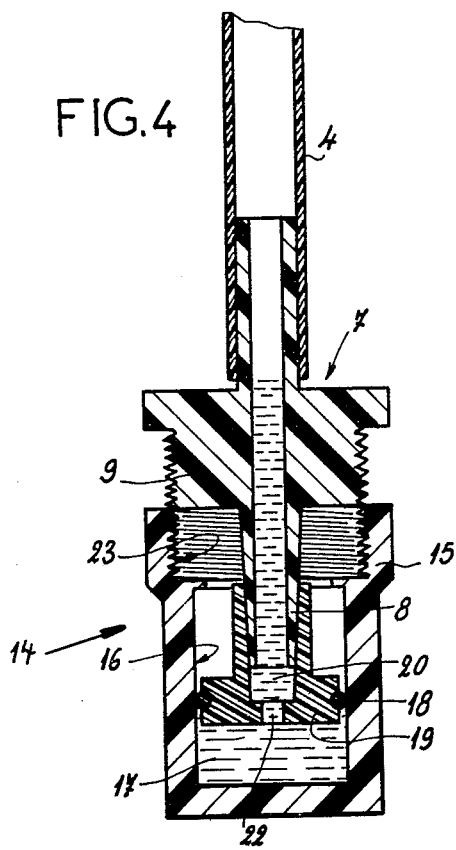
FIGS. 4 and 5 are longitudinal sections showing use of the device of FIG. 3.

As seen in FIG. 1 the device according to the instant invention has a dialysis-solution pouch 2 having a standard sterile connection 5 which is changed several times a day for patients undergoing ambulatory dialysis. A medical tube 3 extends from this connection 5 to another connection 6 carried on the outer free end of a silicone peritoneal catheter 4.

This connection 6, as best shown in FIG. 2, comprises an end fitting 7 fixed on the outer catheter end and formed with a projection 8 having a frustoconical and outwardly tapered outer surface 8' centered on an axis A and an externally threaded neck 9. The other half of the connection 6 is formed by a rigid piece 10 of tube having an inner surface 10' complementary to the outer surface 8' of the projection 8. In addition this rigid tube 10 is provided with an outwardly projecting shoulder 13 engageable by an internally threaded cap 12 that can be screwed onto the threaded neck 9. When this cap 12 is screwed onto the part 7 with the projection 8 lodged in the tube 10, an extremely tight and secure connection 6 is formed that virtually cannot leak or be pulled apart. Normally the elements 10 and 13 come with the tube 3 in a sterile pack, and can be manipulated without touching the inner surfaces that come into contact with the dialysis solution. The end connection 7 cannot be as easily handled without touching its projection 8.

To this end the device 14 shown in FIG. 3 is used. This device has a rigid cylindrical cup 15 forming a reservoir 16 for a body 17 of antiseptic liquid. A piston 19 forms a wall of this reservoir and is provided with a seal 18 radially outwardly engaging the inner wall of the reservoir 16. The face of the piston 19 turned away from the reservoir 16 is formed as a tubular extension 20 having a recess 20' of the same frustoconical shape as the surface 10'. In addition a short small-diameter passage 22 leads from the base of the recess formed by this tubular extension 20 into the reservoir 16. The upper region of the inner wall of the cup 15 is formed with an internal thread, and a plug 24 can be screwed onto this screwthread 23 with the extension 20 received in a cylindrical blind recess 24' in the middle of the plug 24. The screwthread 23 is identical but complementary to the screwthread of the neck 9 of the fitting 7.

In use as shown in FIG. 4 the projection 8 of the fitting 7 is pressed axially down into the recess 20' so as to force the piston 19 downwardly in the reservoir 16. This action forces the liquid 17 up through the small-diameter passage 22 into the catheter 4. To ensure a tight fit the piston 19 is made of a synthetic resin that is somewhat more elastic and easily deformable than the fitting 7, so that the end projection 8 will fit snugly in the tubular projection 20.

Figure 5:
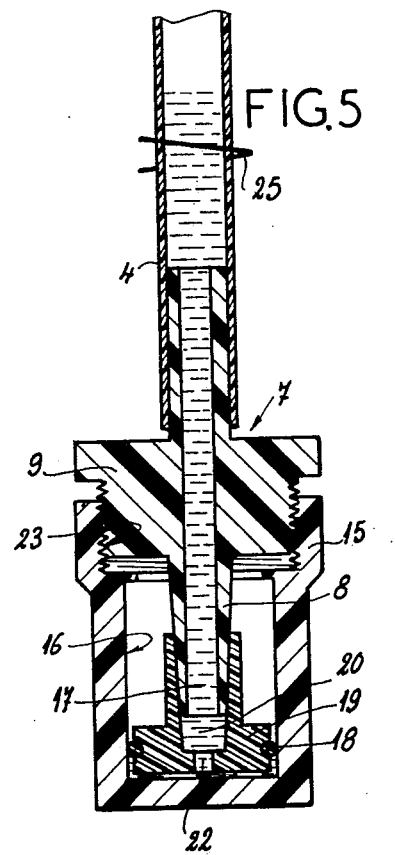

Once the fitting 7 has been forced well into the device 14 the threaded neck 9 can be screwed into the screwthread 23 to make a firm connection, and to further push the piston all the way down in the reservoir into the inner or bottoming position shown in FIG. 5. Meanwhile a standard spring-type tubing clip 25 can be fitted over the catheter downstream of the device 14 to prevent the liquid 17 from rising further than necessary in the catheter 4.

When the fitting 7 is unscrewed and withdrawn the tight friction fit between the projections 8 and 20 will pull the piston 19 back up into the outer position of FIG. 3, thereby causing the volume of the reservoir 16 to increase so that the liquid 17 in the catheter 4 is sucked back into this reservoir 16. In fact virtually every bit of the liquid 17 originally injected into the catheter 4 will be withdrawn from it, so that the fitting 7 can thereafter be inserted right into the tube 10 of a new pouch 2. The operation of fitting the device 14 to the fitting 7 and removing it therefore effectively antisepticizes the fitting 7 and adjoining portion of the catheter 4 wholly automatically.

Figure 6:
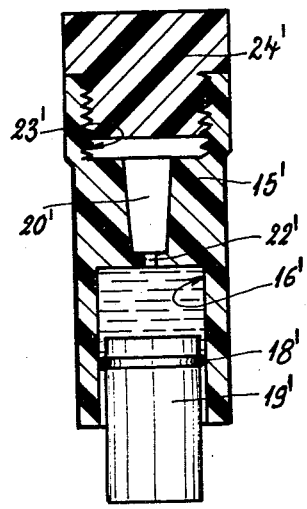

It is also possible to use an arrangement like the one shown in FIG. 6. Here the cap 15', which may be closed by a plug 24' fitting to its internal screwthread 23', has a recess 10' and passage 22' like that of FIG. 3. The reservoir 16' has an outer wall formed by a standard cylindrical piston 19' provided with a seal and manually operable to increase and decrease the reservoir volume.

Similarly in FIG. 7 an arrangement substantially identical to that of FIG. 6 is shown, but having a reservoir 16'' formed by an accordion-shaped elastic wall that can be manually flattened or crushed to squeeze out the liquid in it. A holder or clip may be provided to hold the reservoir 16'' in the flattened position. Normally the natural elasticity of the reservoir 16'' is sufficient that, when released, it can draw back liquid from the catheter end.

Finally FIG. 8 shows how the tube 3 can be provided with a branch 26 having a fitting 7a identical to the fitting 7. Such an arrangement allows the connection 6 to be made in the presence of the antiseptic liquid, and then allows this liquid 17 to be sucked out of the line. With this arrangement the catheter 4 is provided with a clamp 25, as is the tube 3. The fitting 7 is then engaged with the device 14 and pulled off, with the clip 25 ensuring that some of the liquid 17 is left in the fitting 7. This fitting 7 is then inserted into the tube 10 while the branch 26 is in the illustrated position with the piston 19 in the inner or minimum-volume position. Once the connection is made the clamp 25 on the catheter 4 is removed and the device 14 on the branch 26 is actuated to suck the liquid in, thereby antisepticizing the connection 6 internally. In addition FIG. 8 shows a sponge 27 compressed in the bottom of the reservoir 16, such a sponge not only holds the liquid 17 in the reservoir, but also serves as a biasing means or spring to urge the piston 19 into its outer or starting position.

I claim:

1. In combination with a catheter having a tube end provided with an end fitting, an antisepticizing device comprising:
    a cap having a formation of a shape complementary to that of said end fitting and connectable thereto, said cap being formed with a passage having one end communicating with said end fitting and therethrough with said catheter when said end fitting is fitted to said formation;
    a reservoir in said cap having a movable wall, the other end of said passage opening into said reservoir;
    a body of an antiseptic liquid in said reservoir; and
    means automatically effective upon the mounting of the cap on said end fitting for displacing said movable wall of said reservoir and thereby forcing said liquid through said passage into said catheter fitted to said formation.

2. The combination defined in claim 1 wherein said end fitting has a projection and is formed with an external screwthread, said formation being a recess complementary to said projection, said cap being formed with an internal screwthread matable with said external screwthread of said fitting to fit said projection into said formation.

3. The combination defined in claim 2, further comprising a plug having an external thread generally identical to that of said fitting, whereby said cap can be closed by said plug when not in use.

4. The combination defined in claim 2 wherein said passage is of smaller flow cross section than said catheter.

5. The combination defined in claim 2 wherein said reservoir is provided internally with a compressible sponge containing said body of liquid and automatically compressed upon the mounting of said cap on said end fitting.

6. The combination defined in claim 2 wherein said reservoir is provided with a piston constituting said movable wall.

7. The combination defined in claim 2 wherein said movable wall of said reservoir is elastically deformable, whereby flattening of said reservoir pumps the liquid from said reservoir through said passage.

8. The combination defined in claim 2 wherein said end fitting and formation are frustoconical.

9. The combination defined in claim 2 wherein said fitting, formation, and screwthreads are concentric and coaxial when said fitting is screwed into said cap.

10. In combination with a catheter having a tube end provided with an end fitting, an antisepticizing device comprising:
    a cap having a formation of a shape complementary to that of said end fitting and connectable thereto, said cap being formed with a passage having one end communicating with said end fitting and therethrough with said catheter when said end fitting is fitted to said formation;
    a reservoir in said cap having a movable wall, the other end of said passage opening into said reservoir;
    a body of an antiseptic liquid in said reservoir; and
    means for displacing said movable wall of said reservoir and thereby forcing said liquid through said passage into said catheter fitted to said formation, said end fitting having a projection and being formed with an external screwthread, said formation being a recess complementary to said projection, said cap being formed with an internal screwthread matable with said external screwthread of said fitting to fit said projection into said formation, said reservoir being provided with a piston constituting said movable wall, said piston being formed with said formation and passage and being displaceable between an outer position close to said internal screwthread and of maximum reservoir volume and an inner position relatively far from said internal screwthread and of minimum reservoir volume, whereby insertion of said fitting into said formation moves said piston from said outer position to said inner position and vice versa.

* * * * *